United States Patent [19]

Hiraoka et al.

[11] 4,162,251

[45] Jul. 24, 1979

[54] PROCESS FOR THE PREPARATION OF β-LACTAM COMPOUNDS

[75] Inventors: Tetsuo Hiraoka; Takeo Kobayashi, both of Tokyo, Japan

[73] Assignee: Sankyo Company Limited, Tokyo, Japan

[21] Appl. No.: 850,719

[22] Filed: Nov. 11, 1977

Related U.S. Application Data

[62] Division of Ser. No. 779,907, Mar. 21, 1977.

[30] Foreign Application Priority Data

Apr. 5, 1976 [JP] Japan ................................. 51-37958

[51] Int. Cl.$^2$ ................... C07D 499/04; C07D 501/02
[52] U.S. Cl. .................................... 260/239.1; 544/21; 544/26
[58] Field of Search .................. 260/239.1 TB; 544/21

[56] References Cited

U.S. PATENT DOCUMENTS

| | | | |
|---|---|---|---|
| 3,907,788 | 9/1975 | Nudelman | 544/29 |
| 3,960,845 | 6/1976 | Hiraoka et al. | 260/239.1 |
| 4,041,029 | 8/1977 | Firestone et al. | 544/25 |
| 4,053,469 | 10/1977 | Yoshioka et al. | 544/21 |
| 4,119,778 | 10/1978 | Gordon | 544/26 |

OTHER PUBLICATIONS

Baldwin et al., J. Am. Chem. Soc., 95(7) 2401–2403, 04/04/73.
Welch, J. Org. Chem., vol. 41, No. 12, 2220–2222 (1976).

*Primary Examiner*—Donald G. Daus
*Assistant Examiner*—Diana G. Rivers
*Attorney, Agent, or Firm*—Flynn & Frishauf

[57] ABSTRACT

Alkoxylated β-lactam compound useful as an intermediate for various cephalosporin (or penicillin) derivatives which may be prepared by reacting a 7-sulfenylaminocephem compound (or a 6-sulfenylaminopenam compound) with an oxidizing agent or reacting a sulfinylaminocephem compound (or a 6-sulfinylaminopenam compound) with a dehydrated agent to give a sulfenyliminocephem compound (or a 6-sulfenyliminopenam compound) and reacting the latter compound with an alcohol in the presence of a base, an organic acid or a Lewis acid.

4 Claims, No Drawings

PROCESS FOR THE PREPARATION OF β-LACTAM COMPOUNDS

This is a division, of application Ser. No. 779,907, filed Mar. 21, 1977.

This invention relates to new alkoxylated β-lactam compounds and a new process for the preparation thereof.

More particularly, it relates to new alkoxylated β-lactam compounds having the formula

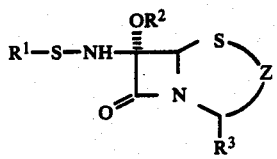

(wherein $R^1$ represents a trihalogenomethyl group or an aromatic hydrocarbyl group optionally substituted with from one to 5 members selected from nitro, cyano, halogen or alkoxycarbonyl, $R^2$ represents an alkyl group, $R^3$ represents carboxyl group or a protected carboxyl group and Z represents a fragment of the formula

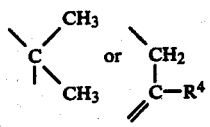

wherein $R^4$ represents alkyl, alkoxy, halogen, carbamoyloxymethyl, acyloxymethyl, 5- or 6-membered heterocyclic thiomethyl optionally having substituted or unsubstituted alkyl) and a pharmaceutically acceptable salt thereof.

In the above formula (I), $R^1$ may be a trihalogenomethyl group, for example, trichloro-, tribromo- or trifluoro methyl; or an aromatic hydrocarbyl group optionally substituted with from one to 5 members selected nitro, cyano, halogen or alkoxycarbonyl, for example, phenyl, o-(m- or p-) nitrophenyl, o-(m- or p-)chlorophenyl, o-(m- or p-)bromophenyl, o-(m- or p-)cyanophenyl, o-(m- or p-)methoxycarbonylphenyl, 2,4-dinitrophenyl, 2,4-dichlorophenyl, 2,4,6-trichlorophenyl, pentachlorophenyl, and naphthyl, preferably pentachlorophenyl, pentabromophenyl and mono- or dinitrophenyl, e.g., o- or p-nitrophenyl, and 2,4-dinitrophenyl.

$R^2$ is preferably an alkyl having 1-4 carbon atoms, for example, methyl, ethyl, n-propyl, isopropyl and n-butyl.

$R^3$ is carboxyl group or a protected carboxyl group such as an alkoxycarbonyl group having 1-4 carbon atoms in the alkyl moiety, e.g., methoxycarbonyl, ethoxycarbonyl, n-propoxycarbonyl, isopropoxycarbonyl, n-butoxycarbonyl, isobutoxycarbonyl, t-butoxycarbonyl, a halogenoalkoxycarbonyl group having 1-4 carbon atoms in the alkyl moiety, e.g., dichloroethoxycarbonyl or trichloroethoxycarbonyl, a benzyloxycarbonyl group optionally substituted with halogen, methoxy or nitro, e.g., benzyloxycarbonyl, p-chlorobenzyloxycarbonyl, p-methoxybenzyloxycarbonyl or p-nitrobenzyloxycarbonyl, diphenylmethyloxycarbonyl group, a trialkylsilyloxycarbonyl group having 1-4 carbon atoms in each alkyl moiety, e.g., trimethylsilyloxycarbonyl or triethylsilyloxycarbonyl, a dialkylhalogenosilyloxycarbonyl group having 1-4 carbon atoms in each alkyl moiety, e.g., dimethylchlorosilyloxycarbonyl or dimethylbromosilyloxycarbonyl, a phenacyloxycarbonyl group optionally substituted with halogen, or methoxy, e.g., p-chlorophenacyloxycarbonyl, p-bromophenacyloxycarbonyl, p-methoxyphenacyloxycarbonyl or an acyloxycarbonyl, e.g., acetoxycarbonyl or benzoyloxycarbonyl, a halogenoacylcarbonyl group, e.g., chloroacetoxycarbonyl or bromoacetoxycarbonyl a dihalogenophosphinooxycarbonyl group, e.g., dichlorophosphinooxycarbonyl or dibromophosphinooxycarbonyl, a dialkylphosphinooxycarbonyl group, e.g., dimethylphosphinoxycarbonyl or an iminocarbonyl group, e.g., 3-oxo-2,3-dihydro-s-triazolo(4,3-a)pyridone-3-ylcarbonyl or saccharylcarbonyl.

$R^3$ is preferably t-butoxycarbonyl, diphenylmethyloxycarbonyl and a phenacyloxycarbonyl group optionally substituted with chlorine or bromine.

$R^4$ is preferably an alkyl having 1-4 carbon atoms, alkoxy having 1-4 carbon atoms, halogen, carbamoyloxymethyl, alkanoyloxymethyl having 1-4 carbon atoms in the alkyl moiety, benzoyloxymethyl or heterocyclic thiomethyl selected from the group consisting of tetrazolyl, 1-alkyltetrazolyl-, 1-carboxyalkyltetrazolyl-, 1-alkoxycarbonylalkyltetrazolyl-, 1-sulfoalkyltetrazolyl-, 1-aminosulfonylalkyl-, 1-mono- or dialkylaminosulfonylalkyltetrazolyl-, 1-aminoalkyltetrazolyl-, 1-mono- or dialkylaminoalkyltetrazolyl-, isoxazolyl-, imidazolyl-, thiazolyl-, triazolyl-, thienyl-, thiadiazolyl-, methylthiadiazolyl-, pyrimidinyl- and pyridylthiomethyl. As the pharmaceutically acceptable salts, there may be mentioned salts of alkali or alkaline earth metals, e.g., sodium, potassium, calcium, aluminum salt, ammonium salt, or salts of organic bases, e.g., triethylamine, dicyclohexylamine, dibenzylamine, dimethylbenzylamine, piperidine or N-ethylpiperidine.

Recently, there have been isolated 7α-methoxycephalosporins from a cultured broth of bacteria belonging to genus Streptomyces (The Journal of the American Chemical Society, 93, 2308; Antimicrobial Agents and Chemotherapy, 2, 122; Japanese Provisional Patent Publication Nos. 26488/74, 30593/74, 42893/74) and various methods for introducing an alkoxy group into the 7-position of cephem nucleus have been developed. These methods may be classified as follows: (a) a method in which a Schiff base of a 7-aminocephem compound is treated with a strong base to produce a carbanion at the 7-position and then the carbanion is directly alkoxylated, or said Schiff base is once halogenated or alkylthiolated and then one of these electrophilic groups is converted into an alkoxy group (Japanese Provisional Patent Publication No. 42691/72, Tetrahedron Letters, 273 and 3505 (1973); Journal of the Organic Chemistry, 38, 943 and 2857 (1973); Journal of the Organic Chemistry, 39, 2794 (1974); (b) a method in which an alkoxy group is introduced after diazotization of a 7-aminocephem compound (The Journal of the American Chemical Society, 94, 1408 (1972); (c) a method in which a 7-acylaminocephem compound is converted after N-chlorination thereof, into a compound having an acylimino group and an alcohol is added thereto (The Journal of the American Chemical Society, 95, 2403 (1973); Tetrahedron Letters, 1311 (1974); Journal of the Organic Chemistry, 38, 1436 (1973); (d) a method in which 7-benzylideneaminocephem compound is oxidized followed by reacting an alcohol (German Patent Laid Open No. 2442540); and (e) a method in which 7β-(α'-halogeno)-cephem compound is reacted with a halogenating agent to give a α-halogenoimminohalide, the product is reacted with an alkali metal alkoxide followed by hydration (German Patent Laid Open No. 2512670). Each of these methods, however, has several deffects. Namely, in method (a), the direct alkoxylation of carbanion at the 7-position of cephem compound gives poor yield and the indirect method, in which an electrophilic group is once introduced and then the group is converted into an alkoxy group, increases the number of steps in the process. In method (b), many steps for reaction is involved, the procedures are complicated and the yield is not good. In method (c), when a anion-forming position exists on a side chain at the 7- or 3-position, the object can not be achieved. In method (d), the 7-alkoxylated-7-benzylideneaminocephem compound obtained can not be directly converted to 7-alkoxylated-7-acylaminocephem compound. In method (e), a certain kind of the starting 7β-(α-halogeno)cephem compound is difficult to be synsesized.

As a result of our earnest studies on alkoxylation of a cephem nucleus at its 7-position or a penam nucleus at its 6-position, we have found and developed an improved method which entirely differs from the prior methods and can be applied to various β-lactam compounds.

It is thus an object of the present invention to provide an alkoxylated β-lactam compound useful as an intermediate for the synthesis of various 7-alkoxylated cephalosporin or 6-alkoxylated penicillin derivatives each having a broad antibacterial spectrum.

It is another object of the present invention to provide a process for the preparation of such an alkoxylated β-lactam compound. Other objects and advantages of this invention will become apparent from the following disclosure of this invention.

According to the present invention, the alkoxylated β-lactam compound having the formula (I) can be prepared by reacting a sulfenylamino β-lactam compound having the formula

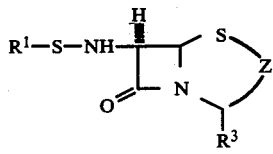

(wherein $R^1$, $R^3$ and Z have the same meanings as defined above)
with an oxidizing agent; or reacting a sulfinylamino β-lactam compound having the formula

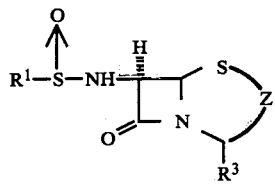

(wherein $R^1$, $R^3$ and Z have the same meanings as defined above)
with a dehydrating agent to give a sulfenylimino β-lactam compound having the formula

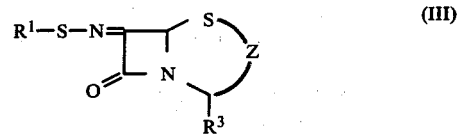

(wherein $R^1$, $R^3$ and Z have the same meanings as defined above)
and reacting the latter compound (III) with an alcohol having the formula $$R^2OH \quad (IV)$$

(wherein $R^2$ has the same meaning as defined above) in the presence of a base, an organic acid or a Lewis acid.

In carrying out the process of this invention, the compound (III) is prepared by reacting the compound (II) with an oxidizing agent. The oxidizing agent in this reaction includes a metal oxide, such as manganese dioxide, potassium permanganate, chromic anhydride, potassium dichromate; lead tetraacetate; potassium nitrosodisulfonate, 2,3-dichloro-5,6-dicyanobenzoquinone; tetrachloro-1,4-benzoquinone; N-chlorosuccinimide; trichloroisocyanuric acid; and sulfuryl chloride. Manganese dioxide can be most preferably employed. The reaction may be preferably carried out in an inert organic solvent under stirring at a temperature of from −100° C. to 100° C. for 30 minutes–3 hours. Suitable solvent is an aprotic solvent, for example, benzene, chloroform, methylene chloride, acetonitrile, dioxane, ethyl acetate. In case where N-chlorosuccinimide, trichloroisocyanuric acid or sulfuryl chloride is used as the oxidizing agent, it is desirable to carry out the reaction in the presence of a tertiary amine, for example, quinoline, diethylaniline, dimethylaniline, pyridine, triethylamine, trimethylamine and diazabicyclooctane. After completion of the reaction, the desired product can be isolated and purified by conventional means.

Alternatively, the compound (III) can be prepared by reacting the compound (II)' with a dehydrating agent in the presence of a base. The dehydrating agent employed in this reaction includes thionyl halides, e.g., thionyl chloride and thionyl bromide; carboxylic acid anhydrides or halides, e.g., acetic anhydride, trifluoroacetic anhydride, acetyl chloride and trifluoroacetyl chloride; organic sulfonic acid anhydrides or halides, e.g., benzenesulfonic anhydride, p-toluenesulfonic anhydride, benzenesulfonyl chloride, p-toluenesulfonyl chloride; phosgene; and phosphrus oxychloride. Thionyl chloride may be most preferably used. The reaction is preferably carried out in an aprotic organic solvent under stirring at a temperature of from −100° C. to a room temperature for 5 minutes–12 hours. Suitable solvent is chloroform, methylene chloride, tetrahydrofuran, ether and ethyl acetate. The base includes a tertiary amine, for example, quinoline, diethylaniline, dimethylaniline, pyridine, triethylamine, trimethylamine and diazabicyclooctane; and an alkali metal carbonate or bicarbonate, for example, sodium carbonate, sodium bicarbonate, potassium carbonate, potassium bicarbonate. After completion of the reaction, the desired product can be isolated and purified by conventional means.

The reaction mixture including the compound (III) can be employed without isolation as a starting material in the next step.

The compound (I) is prepared by reacting the compound (III) with the alcohol (IV) in the presence of a base, an organic acid or a Lewis acid. The base employed in this reaction includes an organic base such as a tertiary amine, for example, quinoline, diethylaniline, dimethylaniline, pyridine, triethylamine, trimethylamine and diazabicyclooctane; and an inorganic base such as an alkali or alkaline earth metal hydroxide, for example, sodium hydroxide, potassium hydroxide, calcium hydroxide; an alkali metal carbonate, for example, sodium carbonate and potassium carbonate, and an alkali metal alkoxide, for example, sodium methoxide, lithium methoxide, potassium methoxide, potassium t-butoxide, sodium t-butoxide. There may be most preferably used an alkali alkoxide having the formula $R^2OM$ (wherein $R^2$ has the same meaning as defined above and M is alkali metal). The organic acid includes methanesulfonic acid, benzenesulfonic acid and p-toluenesulfonic acid and the Lewis acid includes zinc chloride, borontrifluoride etherate.

The reaction may be preferably carried out in an inert organic solvent at a temperature of from $-100°$ C. to $50°$ C., preferably $-40°$ C. to $-20°$ C., for 5 minutes–10 hours. After completion of the reaction, the desired product can be isolated and purified by conventional means.

The compound (II) and (II)', which are used as a starting material in this invention, can be prepared by reacting a compound having the formula

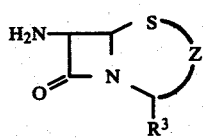
(V)

(wherein $R^3$ and Z have the same meanings as defined above) with a sulfenyl halide having the formula

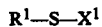

(wherein $R^1$ has the same meaning as defined above and $X^1$ represents a halogen atoms, e.g. chlorine and bromine) or a sulfinyl halide having the formula

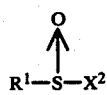

(wherein $R^1$ has the same meaning as defined above and $X^2$ represents a halogen atom, e.g., chlorine and bromine) respectively, in the presence of a hydrogen halide acceptor such as a base or an oxirane. The base includes a tertiary amine, e.g., triethylamine, dimethylamine, pyridine; an alkali metal hydroxide, e.g., sodium hydroxide, potassium hydroxide; and an alkali metal carbonate or bicarbonate, e.g., sodium carbonate, sodium bicarbonate, potassium carbonate and potassium bicarbonate. The oxirane encludes ethylene oxide and propylene oxide. The reaction is preferably carried out in an inert organic solvent, e.g., chloroform, methylene chloride, dioxane, tetrahydrofuran, at a temperature from $-100°$ C. to a room temperature.

The compound (I) obtained in this invention can be converted to various known 7β-acylamino-7α-alkoxycephalosporins or 6β-acylamino-6α-alkoxypenicillins which have excellent antibacterial activities by reaction with organic carboxylic acid halides in an inert solvent.

Alternatively, the compound (I) can be converted to 7β-amino-7α-alkoxycephalosporins or 6β-amino-6α-alkoxypenicillins which are useful as intermediates for β-lactam antibiotics by reaction with a nucleophile such as sodium iodide, thiourea, thiophenol, sodium azide, thioglycolic acid, potassium thiocyanate and sodium thiosulfate, hexamethylphosphorous triamide. The following examples and referential examples are given for purpose of illustrating of this invention. It is to be understood that these examples and referential examples should not be construed as limiting the scope of this invention.

Examples 1 to 4 illustrate the preparation of the compound (I) from the compound (III).

Examples 5 to 14 illustrate the preparation of the compound (I) from the compound (II) or (II)' via the compound (III).

Referential examples 1 to 5 illustrate the preparation of the compound (II) and (II)' from the compound (V).

Referential example 6 to 9 illustrate the preparation of the compound (VI) from the compound (I).

Referential examples 4 to 6 illustrate the preparation of the compound (VII) from the compound (I).

Reaction sequence in this invention may be schematically shown as follows:

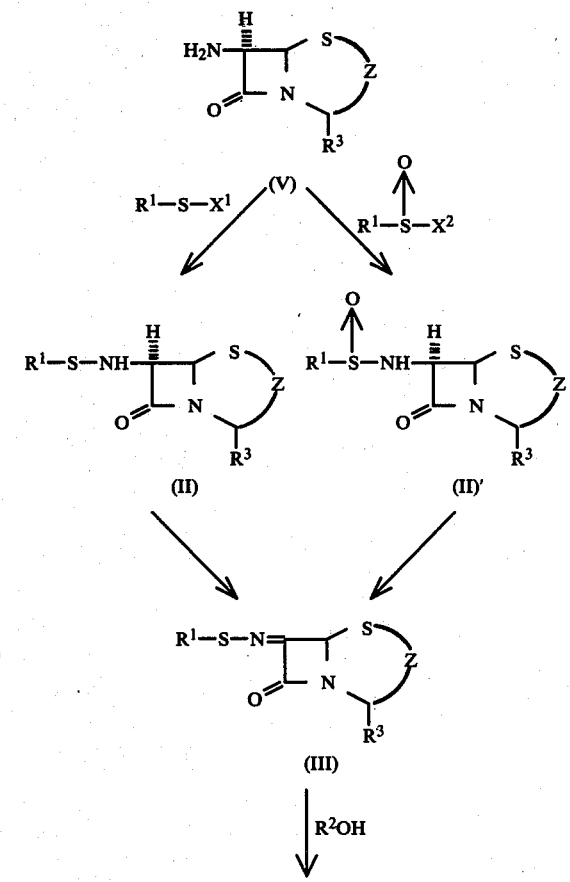

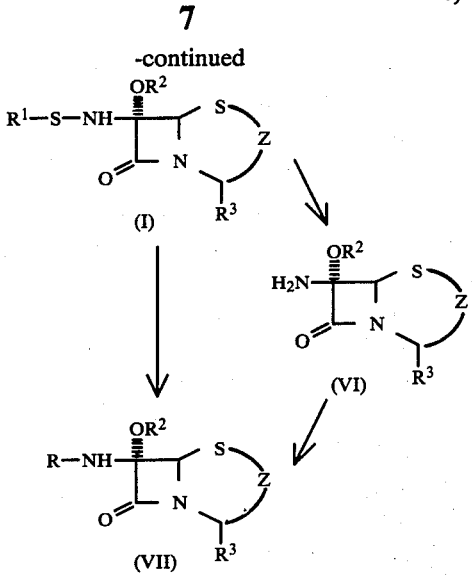

$R^1$, $R^2$, $R^3$, Z, $X^1$ and $X^2$ have the same meanings as defined above and R represents an acyl group.

EXAMPLE 1

7α-Methoxy-3-methyl-7β-orthonitrophenylsulfenylamino-3-cephem-4-carboxylic acid tert-butyl ester In 60 ml. of anhydrous methanol was suspended 1.72 g. of 3-methyl-7-orthonitrophenylsulfenylimino-3-cephem-4-carboxylic acid tert-butyl ester. To the suspension was added under stirring at −78° C. a solution of lithium methoxide which was prepared from 170 mg. (24.5 mmol.) of metallic lithium and 24 ml. of anhydrous methanol. After stirring at −78° C. for 30 minutes, 70 ml. of anhydrous tetrahydrofuran was gradually added to the mixture and the reaction mixture was further stirred for 3.5 hours at −78° C. to produce a transparent solution. After 2.0 ml. of acetic acid was added to complete the reaction and then 50 ml. of water was added to the reaction mixture, the thus obtained mixture was extracted three times with 100 ml. of ethyl acetate. After washing with water and drying, the solvent was removed by evaporation under reduced pressure to obtain a crude product. The crude product was submitted to purification by column-chromatography in which silica gel was used as a packing and a mixture of benzene-ethyl acetate (10:1) was used as an eluent to isolate 1.17 g. of 7α-methoxy-3-methyl-7β-orthonitrophenylsulfenylamino-3-cephem-4-carboxylic acid tert-butyl ester melting at 149°–150° C. Infrared Spectrum (Nujol):3300, 1765 $cm^{-1}$.

Nuclear Magnetic Resonance Spectrum ($CDCl_3$) δppm:
1.50 (9H, singlet), 2.12 (3H, singlet)
3.18 and 3.39 (2H, AB-quartet, J=18 Hz)
3.57 (3H, singlet), 4.30 (1H, singlet)
4.90 (1H, singlet), 7.12–8.35 (4H, multiplet).

EXAMPLE 2

7α-Methoxy-3-methyl-7β-(2',4'-dinitrophenyl)sulfenylamino-3-cephem-4-carboxylic acid tert-butyl ester In 30 ml. of anhydrous methanol was suspended 1.35 g. of 3-methyl-7-(2',4'-dinitrophenyl)sulfenylimino-3-cephem-4-carboxylic acid tert-butyl ester. To the suspension was added under stirring at −78° C. a solution of lithium methoxide which was prepared from 102 mg. of metallic lithium and 12 ml. of anhydrous methanol. After stirring at −78° C. for 30 minutes, 35 ml. of anhydrous tetrahydrofuran was gradually added to the mixture and the reaction mixture was further stirred for 3.5 hours at −78° C. to produce a transparent solution. After 1.0 ml. of acetic acid was added to complete the reaction and then 25 ml. of water was added to the reaction mixture, the thus obtained mixture was extracted three times with 50 ml. of ethyl acetate. After washing with water and drying, the solvent was removed by evaporation under reduced pressure to obtain a crude product. The crude product was submitted to purification by columnchromatography in which silica gel was used as a packing and a mixture of benzene-ethyl acetate (10:1) was used as an eluent to isolate 1.20 g. of 7α-methoxy-3-methyl-7β-(2',4'-dinitrophenyl)sulfenylamino-3-cephem-4-carboxylic acid tert-butyl ester.

Infrared Spectrum (Nujol): 3300, 1780 $cm^{-1}$.
Nuclear Magnetic Resonance Spectrum ($CDCl_3$) δ ppm:
1.49 (9H, singlet), 2.12 (3H, singlet)
3.20 and 3.40 (2H, AB-quartet, J=18 Hz)
3.58 (3H, singlet), 4.58 (1H, singlet)
4.93 (1H, singlet), 8.35–9.08 (3H, multiplet).

EXAMPLE 3

7α-Methoxy-3-acetoxymethyl-7β-orthonitrophenylsulfenylamino-3-cephem-4-carboxylic acid benzhydryl ester In a mixture of 60 ml. of methanol and 40 ml. of benzene was dissolved 515 mg. of 3-acetoxymethyl-7-orthonitrophenylsulfenylimino-3-cephem-4-carboxylic acid benzhydryl ester. To the solution was added with stirring at room temperature 155 mg. of paratoluenesulfonic acid hydrate to effect reaction. After 30 minutes, a saturated solution of sodium bicarbonate was added to stop the reaction and the reaction mixture was extracted three times with ethyl acetate. After washing with water and drying, the solvent was removed by evaporation under reduced pressure to obtain a crude product. The crude product was submitted to purification by column-chromatography in which a mixture of benzene-ethyl acetate (10:1) was used as an eluent and silica gel was used as a packing to isolate 388 mg. of 7α-methoxy-3-acetoxymethyl-7β-orthonitrophenylsulfenylamino-3-cephem-4-carboxylic acid benzhydryl ester.

EXAMPLE 4

6α-Methoxy-6β-orthonitrophenylsulfenylaminopenicillanic acid parabromophenacyl ester In 15 ml. of anhydrous methanol was suspended 558 mg. of 6-orthonitrophenylsulfenyliminopenicillanic acid parabromophenacyl ester. To the suspension was added under stirring at −78° C. a solution of lithium methoxide which was prepared from 36.2 mg. of metallic lithium and 6 ml of anhydrous methanol. After stirring at −78° C. for 30 minutes, 18 ml. of anhydrous tetrahydrofuran was gradually added to the mixture and the reaction mixture was further stirred for 3.5 hours at −78° C. to produce a transparent solution. After 0.5 ml. of acetic acid was added to complete the reaction and then 12 ml. of water was added to the reaction mixture, the thus obtained mixture was extracted three times with 25 ml. of ethyl acetate. After washing with water and drying, the solvent was removed by evaporation under reduced pressure to obtain a crude product. Subsequently, the crude product was submitted to purification by preparative silica gel thin-layer-chromatography (thickness: 0.2 cm., 20×40 cm, development system: benzene-ethyl acetate (10:1)) and a component having a Rf value of 0.4 was isolated to obtain 182 mg. of 6α-methoxy-6β-orthonitrophenylsulfenylaminopenicillanic acid parabromophenacyl ester melting at 148°–150° C.

Infrared Spectrum (Nujol): 3300, 1790 cm$^{-1}$.

Nuclear Magnetic Resonance Spectrum (CDCl$_3$) δ ppm:
  1.68 (6H, singlet), 3.53 (3H, singlet)
  4.30 (1H, singlet), 4.80 (1H, singlet)
  5.38 (2H, singlet), 5.45 (1H, singlet)
  7.23–8.38 (8H, multiplet).

EXAMPLE 5

6α-Methoxy-6β-orthonitrophenylsulfenylaminopenicillanic acid parabromophenacyl ester In 100 ml. of benzene was dissolved 2.0 g. of 6β-orthonitrophenylsulfenylaminopenicillanic acid parabromophenacyl ester. To the solution was added 60.0 g. of active manganese dioxide with stirring at room temperature and the reaction mixture was stirred further for 1 hour at room temperature. After completion of the reaction, insoluble substance was removed by filtration and the solvent was removed by evaporation under reduced pressure to obtain 1.38 g. of 6-orthonitrophenylsulfenyliminopenicillanic acid parabromophenacyl ester.

Infrared Spectrum (Nujol): 1780 cm$^{-1}$

Nuclear Magnetic Resonance Spectrum (CDCl$_3$) δ ppm:
  1.65 (3H, singlet), 1.72 (3H, singlet).
  4.80 (1H, singlet), 5.43 (2H, singlet).
  5.97 (1H, singlet), 7.22–8.53 (8H, multiplet).

The thus obtained 6-orthonitrophenylsulfenyliminopenicillanic acid parabromophenacyl ester was treated as in Example 4 to give 6α-methoxy-6β-orthonitrophenylsulfenylaminopenicillanic acid parabromophenacyl ester.

EXAMPLE 6

7α-Methoxy-3-methyl-7β-paranitrophenylsulfenylamino-3-cephem-4-carboxylic acid tert-butyl ester In 100 ml. of benzene was dissolved 2.0 g of 3-methyl-7β-paranitrophenylsulfenylamino-3-cephem-4-carboxylic acid tert-butyl ester. To the solution was added 60.0 g. of active manganese dioxide with stirring at room temperature and the reaction mixture was stirred further for 1 hour at room temperature. After completion of the reaction, insoluble substance was removed by filtration and the solvent was removed by evaporation under reduced pressure to obtain 1.65 g. of 3-methyl-7-paranitrophenylsulfenylimino-3-cephem-4-carboxylic acid tert-butyl ester melting at 169°–170° C.

Infrared Spectrum (Nujol): 1790 cm$^{-1}$.

Nuclear Magnetic Resonance Spectrum (CDCl$_3$) δ ppm:
  1.58 (9H, singlet), 2.15 (3H, singlet)
  3.23 and 3.53 (2H, AB-quartet, J=18 Hz)
  5.37 (1H, singlet), 7.55–8.40 (4H, multiplet).

In 50 ml. of anhydrous methanol was suspended 2.70 g. of thus obtained 3-methyl-7-paranitrophenylsulfenylimino-3-cephem-4-carboxylic acid tert-butyl ester. To the suspension was added under stirring at −78° C. a solution of lithium methoxide which was prepared from 231 mg. of metallic lithium and 20 ml. of anhydrous methanol. After stirring at −78° C. for 30 minutes, 70 ml. of anhydrous tetrahydrofuran was gradually added to the mixture and the reaction mixture was further stirred at −78° C. for 3.5 hours to produce a transparent solution. After 2.40 ml. of acetic acid was added to complete the reaction and then 70 ml. of water was added to the reaction mixture, the thus obtained mixture was extracted three times with 150 ml. of ethyl acetate. After washing with water and drying, the solvent was removed by evaporation under reduced pressure to obtain a crude product. The crude product was submitted to purification by columnchromatography in which silica gel was used as a packing and a mixture of benzene-ethyl acetate (10:1) was used as an eluent to isolate 1.45 g. of 7α-methoxy-3-methyl-7β-paranitrophenylsulfenylamino-3-cephem-4-carboxylic acid tert-butyl ester melting at 120°–121° C.

Infrared Spectrum (Nujol): 3300, 1765 cm$^{-1}$.

Nuclear Magnetic Resonance Spectrum (CDCl$_3$) δ ppm:
  1.52 (9H, singlet), 2.12 (3H, singlet)
  3.15 and 3.38 (2H, AB-quartet, J=18 Hz)
  3.53 (3H, singlet), 4.48 (1H, singlet)
  4.88 (1H, singlet), 7.27–8.28 (4H, multiplet).

EXAMPLE 7

7α-Methoxy-3-methyl-7β-paranitrophenylsulfenylamino-3-cephem-4-carboxylic acid tert-butyl ester In 3 ml. of carbon tetrachloride was suspended 205 mg. of 3-methyl-7β-paranitrophenylsulfenylamino-3-cephem-4-carboxylic acid tert-butyl ester. To the suspension was added with stirring 0.08 ml. of triethylamine and then 73.8 mg. of N-chlorosuccinimide and the reaction mixture was stirred at 40° C. for 1 hour. After adding further 0.04 ml. of triethylamine and 42.5 mg. of N-chlorosuccinimide, the mixture was stirred at 40° C. for 30 minutes. After completion of the reaction, insoluble substance was removed by filtration and the solvent was removed by evaporation under reduced pressure to obtain a crude product. The crude product was submitted to preparative silica gel thin-layer-chromatography (thickness: 0.2 cm., 20×20 cm., development system: benzene-ethyl acetate (10:1)) to isolate 134 mg. of 3-methyl-7-paranitrophenylsulfenylimino-3-cephem-4-carboxylic acid tert-butyl ester.

The thus obtained compound was reacted, as in Example 5, with lithium methoxide to give 7α-methoxy-3-methyl-7β-paranitrophenylsulfenylamino-3-cephem-4-carboxylic acid tert-butyl ester.

EXAMPLE 8

7α-Methoxy-3-methyl-7β-orthonitrophenylsulfenylamino-3-cephem-4-carboxylic acid tert-butyl ester (a) In 100 ml. of benzene was dissolved 2.0 g. of 3-methyl-7β-orthophenylsulfenylamino-3-cephem-4-carboxylic acid tert-butyl ester. To the solution was added 60.0 g. of active manganese dioxide with stirring at room temperature and the reaction mixture was stirred further for 1 hour at room temperature. After completion of the reaction, insoluble substance was removed by filtration and the solvent was removed by evaporation under reduced pressure to obtain 1.72 g. of 3-methyl-7-orthonitrophenylsulfenylimino-3-cephem-4-carboxylic acid tert-butyl ester melting at 183°–184° C.

Infrared Spectrum (Nujol): 1780 cm$^{-1}$.

Nuclear Magnetic Resonance Spectrum (CDCl$_3$) δ ppm:

1.60 (9H, singlet), 2.16 (3H, singlet)
3.27 and 3.58 (2H, AB-quartet, J=19 Hz)
5.47 (1H, singlet), 7.33–8.62 (4H, multiplet).

(b) To a solution of 70 mg. of 3-methyl-7β-orthonitrophenylsulfinylamino-3-cephem-4-carboxylic acid t-butyl ester in 1 ml. of tetrahydrofuran and 2.5 ml. of chloroform were added successively 93 mg. of quinoline in 0.45 ml. of chloroform and 29 mg. of thionyl chloride in 0.2 ml. of chloroform. The reaction mixture was stirred at −30° C. for 1 hour and at 0° C. for 1 hour. Further 93 mg. of quinoline in 0.45 ml. of chloroform and 29 mg. of thionyl chloride in 0.2 ml. of chloroform were added to the solution and stirring at 0° C. was continued overnight. To the resulting reaction mixture were added 5 ml. of saturated sodium bicarbonate solution and 50 ml. of ethyl acetate, and the organic phase was separated. The aqueous layer was extracted with 15 ml. of ethyl acetate. The combined organic extracts were dried over sodium sulfate and evaporated to give an oil which contained quinoline. This oil was purified by column chromatography using silica gel to afford 36 mg. of pure 3-methyl-7-ortho-nitrophenylsulfenylimino-3-cephem-4-carboxylic acid t-butyl ester, which was identical with the authentic sample obtained in the above (a).

3-Methyl-7-orthonitrophenylsulfenylimino-3-cephem-4-carboxylic acid tert-butyl ester thus obtained was treated as in Example 1 to obtain 7α-methoxy-3-methyl-7β-orthonitrophenylsulfenylamino-3-cephem-4-carboxylic acid tert-butyl ester.

EXAMPLE 9

7α-Methoxy-3-methyl-7β-orthonitrophenylsulfenylamino-3-cephem-4-carboxylic acid tert-butyl ester In 15 ml. of carbon tetrachloride was suspended 656 mg. of 3-methyl-7β-orthonitrophenylsulfenylamino-3-cephem-4-carboxylic acid tert-butyl ester. To the suspension was added with stirring under ice cooling 0.35 ml. of triethylamine and then 585 mg. of trichloroisocyanuric acid, and the reaction mixture was stirred at 0° C. for 1.5 hours. After completion of the reaction, insoluble substance was filtered off and the solvent of the filtrate was removed under reduced pressure to obtain a crude product. The crude product was submitted to preparative silica gel thin-layer chromatography (thickness: 0.2 cm., 20×20 cm., development system: benzene-ethyl acetate (10:1)) to isolate 145 mg. of 3-methyl-7β-orthonitrophenylsulfenylimino-3-cephem-4-carboxylic acid tert-butyl ester. The product thus isolated was treated as in Example 1 to obtain 7α-methoxy-3-methyl-7β-orthonitrophenylsulfenylamino-3-cephem-4-carboxylic acid tert-butyl ester.

EXAMPLE 10

3-Acetoxymethyl-7α-methoxy-7β-orthonitrophenylsulfenylamino-3-cephem-4-carboxylic acid benzhydryl ester (a) In 100 ml. of benzene was dissolved 2.0 g. of 3-acetoxymethyl-7β-orthonitrophenylsulfenylamino-3-cephem-4-carboxylic acid benzhydryl ester. To the solution was added 70 g. of active manganese dioxide with stirring at room temperature and the reaction mixture was stirred for 1.0 hour at room temperature. After completion of the reaction, insoluble substance was removed by filtration and the solvent was removed by evaporation under reduced pressure to obtain 1.40 g. of 3-acetoxymethyl-7-orthonitrophenylsulfenylimino-3-cephem-4-carboxylic acid benzhydryl ester melting at 134°–135° C.

Infrared Spectrum (Nujol): 1780 cm$^{-1}$.

Nuclear Magnetic Resonance Spectrum (CDCl$_3$) δ ppm:
2.01 (3H, singlet)
3.39 and 3.65 (2H, AB-quartet, J=19 Hz)
4.85 and 5.08 (2H, AB-quartet, J=14 Hz)
5.47 (1H, singlet), 7.08 (1H, singlet)
7.25–8.60 (14H, multiplet).

(b) To a solution of 122 mg. of 3-acetoxymethyl-7β-ortho-nitrophenylsulfinylamino-3-cephem-4-carboxylic acid benzhydryl ester in 3 ml. of chloroform were added successively 233 mg. of quinoline in 0.5 ml. of chloroform and 72 mg. of thionyl chloride in 1 ml. of chloroform under ice-water cooling. The reaction mixture was stirred at 0° C. for 1.5 hour. To the resulting solution were added 10 ml. of saturated sodium bicarbonate solution and 70 ml. of ethyl acetate, and the mixture was well stirred. The organic layer was separated and washed with saturated sodium chloride solution twice. After drying over sodium sulfate the solvents were evaporated under reduced pressure to give an oil, which was chromatographed on 4 g. of silica gel. Elution with benzene and evaporation afforded 37 mg. of 3-acetoxymethyl-7-ortho-nitrophenylsulfenylimino-3-cephem-4-carboxylic acid benzhydryl ester, which was identical with the authentic sample obtained in the above (a).

3-Acetoxymethyl-7-orthonitrophenylsulfenylimino-3-cephem-4-carboxylic acid benzhydryl ester thus obtained was treated as in Example 3 to give 3-acetoxymethyl-7α-methoxy-7β-orthonitrophenylsulfenylamino-3-cephem-4-carboxylic acid benzhydryl ester.

EXAMPLE 11

7α-Methoxy-3-methyl-7β-(2′,4′-dinitrophenyl)sulfenylamino-3-cephem-4-carboxylic acid tert-butyl ester In 100 ml. of benzene was dissolved 2.0 g. of 3-methyl-7β-(2′,4′-dinitrophenyl)sulfenylamino-3-cephem-4-carboxylic acid tert-butyl ester. To the solution was added 60.0 g. of active manganese dioxide with stirring at room temperature and the reaction mixture was stirred further for 1 hour at room temperature. After completion of the reaction, insoluble substance was removed by filtration and the solvent was removed by evaporation under reduced pressure to obtain 1.35 g. of 3-methyl-7-(2′,4′-dinitrophenyl)sulfenylimino-3-cephem-4-carboxylic acid tert-butyl ester melting at 187°–188° C.

Infrared Spectrum (Nujol): 1790 cm$^{-1}$.

Nuclear Magnetic Resonance Spectrum (CDCl$_3$) δ ppm:
1.58 (9H, singlet), 2.18 (3H, singlet)
3.25 and 3.60 (2H, AB-quartet, J=18.5 Hz)
5.45 (1H, singlet), 8.38–9.23 (3H, multiplet).

Thus obtained 3-methyl-7β-(2′,4′-dinitrophenyl)sulfenylimino-3-cephem-4-carboxylic acid tert-butyl ester was treated as in Example 2 to give 7α-methoxy-3-methyl-7β-(2′,4′-dinitrophenyl)sulfenylamino-3-cephem-4-carboxylic acid tert-butyl ester.

EXAMPLE 12

7α-Methoxy-3-methyl-7β-pentachlorophenylsulfenylamino-3-cephem-4-carboxylic acid t-butyl ester To a solution of 500 mg. of 3-methyl-7β-pentachlorophenylsulfenylamino-3-cephem-4-carboxylic acid t-butyl ester in 25 ml. of benzene was added portion wise 15 g. of activated manganese dioxide. The reaction mixture was stirred at room temperature for 1 hour. Then further 10 g. of manganese dioxide was added and stirring was continued for 1 hour. The solid substance was filtered off and washed well with benzene. The combined filtrate was evaporated under reduced pressure and the residue was purified by preparative tlc to afford 88 mg. of 3-methyl-7-pentachlorophenylsulfenylimino-3-cephem-4-carboxylic acid t-butyl ester, which melted at 195°–197° C.

Nuclear Magnetic Resonance Spectrum (CDCl$_3$) δ ppm:
1.56 (9H, singlet), 2.10 (3H, singlet)
3.22 and 3.45 (2H, AB-quartet, J=18 Hz)
5.28 (1H, singlet).

Infrared Spectrum (Nujol): 1760, 1705 cm$^{-1}$

To a solution of 55 mg. of 3-methyl-7-pentachlorophenylsulfenylimino-3-cephem-4-carboxylic acid t-butyl ester in 3 ml. of chloroform and 2.0 ml. methanol was added a solution of 0.76 mg. of lithium in 1 ml. of methanol at −78° C. The reaction mixture was stirred at −40° C. for 45 minutes and at −20° C. for 1.5 hours. To the resulting solution were added 8 mg. of acetic acid in 1.5 ml. of chloroform and 50 ml. of ethyl acetate, which was washed with sodium bicarbonate solution and saturated sodium chloride solution. After drying over sodium sulfate the organic solvents were removed under diminished pressure. The residue was purified by preparative tlc to give 29 mg. of 7α-methoxy-3-methyl-7β-pentachlorophenylsulfenylamino-3-cephem-4-carboxylic acid t-butyl ester as a foam.

Nuclear Magnetic Resonance Spectrum (CDCl$_3$) δ ppm:
1.49 (9H, singlet), 2.08 (3H, singlet)
3.23 (3H, singlet)
3.21 and 3.31 (2H, AB-quartet, J=18 Hz)
4.79 (1H, singlet), 4.89 (1H, singlet).

EXAMPLE 13

7α-Methoxy-3-methyl-7β-paranitrophenylsulfenylamino-3-cephem-4-carboxylic acid tert-butyl ester In 5 ml. of methylene chloride was dissolved 200 mg. of 3-methyl-7β-paranitrophenylsulfinylamino-3-cephem-4-carboxylic acid tert-butyl ester. To the solution was added with stirring at −78° C. 0.20 ml. of triethylamine and then 0.10 ml. of thionyl chloride. After stirring the reaction mixture at −78° C. for 1.5 hours, 20 ml. of methylene chloride was added thereto. After the reaction mixture was washed with a saturated solution of sodium bicarbonate and with water, and dried, the solvent was removed by evaporation under reduced pressure to obtain a crude product. The crude product was purified by preparative silica gel thin-layer chromatography (thickness: 0.2 cm., 20×20 cm., development system: benzene-ethyl acetate (10:1)) to isolate 77 mg. of 3-methyl-7-paranitrophenylsulfenylimino-3-cephem-4-carboxylic acid tert-butyl ester. The thus obtained compound was treated as in Example 6 to give 7α-methoxy-3-methyl-7β-paranitrophenylsulfenylamino-3-cephem-4-carboxylic acid tert-butyl ester.

EXAMPLE 14

7α-Methoxy-3-(1-methyl-1H-tetrazol-5-yl)thiomethyl-7β-ortho-nitrophenylsulfenylamino-3-cephem-4-carboxylic acid To a suspension of 200 mg. of 3-(1-methyl-1H-tetrazol-5-yl)thiomethyl-7β-ortho-nitrophenylsulfinylamino-3-cephem-4-carboxylic acid in 5 ml. of chloroform was added 44 mg. of triethylamine. After 5 minutes stirring 52 mg. of chlorotrimethylsilane was added under ice-water cooling and the reaction mixture was stirred at room temperature for 30 minutes. The resulting solution was cooled to −40° C. and 310 mg. of quinoline in 1 ml. of chloroform was added, followed by the addition of 119 mg. of thionyl chloride. The reaction mixture was stirred at −30° C. for 2 hours, then a solution of 36 mg. of lithium in 2 ml. of methanol was added and stirring at −30° C. was continued for 2 hours. The reaction was quenched by the addition of 0.3 ml. of acetic acid. Phosphate buffer (pH:7.8, 50 ml.) was added and the aqueous layer was separated and washed once with ether. The solution was acidified to pH 3.0 with diluted hydrochloric acid and extracted with ethyl acetate. The combined extracts were washed with saturated sodium chloride solution, dried over magnesium sulfate. Evaporation of the solvent under reduced pressure gave 200 mg. of crude 7α-methoxy-3-(1-methyl-1H-tetrazol-5-yl)-thiomethyl-7β-ortho-nitrophenylsulfenylamino-3-cephem-4-carboxylic acid. For identification, this acid was converted to the corresponding benzhydryl ester as follows. The crude acid was dissolved in 50 ml. of ethyl acetate and treated with 194 mg. of diphenyldiazomethane. The solution was stirred at room temperature overnight and evaporated under diminished pressure. The residue was purified by preparative tlc using silica gel plate which was developed with benzene-ethyl acetate (4:1) to give 58 mg. of pure 7α-methoxy-3-(1-methyl-1H-tetrazol)thiomethyl-7β-orthonitrophenylsulfenylamino-3-cephem-4-carboxylic acid benzhydryl ester as a foam.

Infrared Spectrum (Nujol): 3300, 1785, 1720 cm$^{-1}$.

Nuclear Magnetic Resonance Spectrum (CDCl$_3$) δ ppm:
3.50 (3H, singlet), 3.60 (2H, singlet),
3.76 (3H, singlet)
4.20 and 4.46 (2H, AB-quartet, J=14 Hz)
4.40 (1H, singlet), 4.92 (1H, singlet)
6.90 (1H, singlet), 7.05–8.36 (14H, multiplet).

REFERENTIAL EXAMPLE 1

3-Methyl-7β-orthonitrophenylsulfenylamino-3-cephem-4-carboxylic acid tert-butyl ester In 100 ml. of anhydrous tetrahydrofuran was dissolved 5.40 g. of 7β-amino-3-methyl-3-cephem-4-carboxylic acid tert-butyl ester. To the solution was added with stirring under ice cooling 2.80 ml. of triethylamine and 40 ml. of an anhydrous tetrahydrofuran solution containing 3.79 g. of orthonitrophenylsulfenyl chloride was added after 30 minutes. The mixture was stirred for 2 hours under ice cooling and further for 3 hours at room temperature. After completion of the reaction, triethylamine hydrochloride produced was filtered off and the filtrate was concentrated. The residue was purified by coloumnchromatography in which silica gel was used as a packing and a mixture of benzene-ethyl acetate (10:1) was used as an eluent to isolate 7.20 g. of 3-methyl-7β-orthonitrophenylsulfenylamino-3-cephem-4-carboxylic acid tert-butyl ester melting at 171°–172° C.
  Infrared Spectrum (Nujol): 3275, 1775 cm$^{-1}$.
  Nuclear Magnetic Resonance Spectrum (CDCl$_3$) δ ppm:
  1.50 (9H, singlet), 2.08 (3H, singlet)
  3.22 and 3.60 (2H, AB-quartet, J=18 Hz)
  4.73 (1H, quartet, J=5, 9 Hz)
  3.67 (1H, doublet, J=9 Hz), 4.99 (1H, doublet, J=5 Hz)
  7.17–8.37 (4H, multiplet).

REFERENTIAL EXAMPLE 2

6β-orthonitrophenylsulfenylaminopenicillanic acid parabromophenacyl ester

In 225 ml. of anhydrous tetrahydrofuran was suspended 11.3 g. of 6β-aminopenicillanic acid parabromophenacyl ester hydrochloride. To the solution was added with stirring under ice cooling 7.0 ml. of triethylamine, and 10 ml. of an anhydrous tetrahydrofuran solution containing 4.74 g. of orthonitrophenylsulfenylchloride was added after 30 minutes. The mixture was stirred for 2 hours under ice cooling and further for 3 hours at room temperature. After completion of the reaction, triethylamine hydrochloride produced was filtered off and the filtrate was concentrated. The residue was purified by coloumnchromatography in which silica gel was used as a packing and a mixture of benzene-ethyl acetate (10:1 V/V) was used as an eluent to isolate 17.8 g. of 6β-orthonitrophenylsulfenylaminopenicillanic acid parabromophenacyl ester.
  Infrared Spectrum (Nujol):3250, 1780 cm$^{-1}$.
  Nuclear Magnetic Resonance Spectrum (CDCl$_3$) δ ppm:
  1.73 (3H, singlet), 1.78 (3H, singlet)
  3.67 (1H, doublet, J=10 Hz), 4.62 (1H, singlet)
  4.67 (1H, quartet, J=4 and 10 Hz)
  5.30 and 5.55 (2H, AB-quartet, J=16 Hz)
  5.65 (1H, doublet, J=4 Hz), 7.18–8.42 (8H, multiplet).

REFERENTIAL EXAMPLE 3

3-Methyl-7β-ortho-nitrophenylsulfinylamino-3-cephem-4-carboxylic acid t-butyl ester A solution of 590 mg. of ortho-nitrophenylsulfinyl chloride in 3 ml. of tetrahydrofuran was added to a solution of 540 mg. of 7-amino-3-methyl-3-cephem-4-carboxylic acid t-butyl ester and 253 mg. of triethyl amine in 7 ml. of tetrahydrofuran at 0° C. The reaction mixture was stirred at 0° C. for 2 hours. The solution was diluted with 100 ml. of ethyl acetate which was washed with water, sodium bicarbonate solution and saturated sodium chloride solution. After drying over sodium sulfate the solvents were evaporated under reduced pressure to afford an oil. This crude oil was purified by column chromatography on silica gel to give 739 mg. of 3-methyl-7β-ortho-nitrophenylsulfinylamino-3-cephem-4-carboxylic acid t-butyl ester as an oil, which is a mixture of two diastereoisomers due to a sulfinyl group in the 7β-side chain.
  Nuclear Magnetic Resonance Spectra (CDCl$_3$+D$_2$O) δ ppm:
  1.46 and 1.56 (9H, two singlets)
  2.01 and 2.06 (3H, two singlets), 3.07 and 3.25;
  3.16 and 3.43 (2H, two kinds of AB-quartet, J=18 Hz),
  4.34 (1H, doublet, J=4.5 Hz), 5.27 (1H, doublet, J=4.5 Hz), 7.55–8.42 (4H, multiplet).

REFERENTIAL EXAMPLE 4

3-(1-Methyl-1H-tetrazol-5-yl)thiomethyl-7β-orthonitrophenylsulfinylamino-3-cephem-4-carboxylic acid In 15 ml. of methylenchloride was suspended 986 mg. of 7β-amino-3-(1-methyl-1H-tetrazol-5-yl)thiomethyl-4-carboxylic acid, to which was added 0.5 ml. of triethylamine. After 5 minutes stirring 0.5 ml. of chlorotrimethylsilane was added under ice-water cooling, and stirring was continued at room temperature for 1 hour. The solution was cooled to −40° C. and 0.57 ml. of dimethylaniline and 920 mg. of ortho-nitrobenzenesulfinyl chloride in 4.5 ml. of methylene chloride were added. The reaction mixture was stirred at 0° C. for 30 minutes and at 0° C. for 2 hours. To the resulting solution was added 50 ml. of phosphate buffer (pH 7.8) and aqueous layer was separated, which was once washed with ether. The aqueous solution was acidified to pH 2.7 with diluted hydrochloric acid and extracted with ethyl acetate three times. The combined extracts were washed with saturated sodium chloride solution once, dried over magnesium sulfate and evaporated under reduced pressure. The residue was washed with a small amount of ether to give 531 mg. of 3-(1-methyl-1H-tetrazol-5-yl)thiomethyl-7β-ortho-nitrophenylsulfinylamino-3-cephem-4-carboxylic acid as powder. This compound is a mixture of two diastereoisomers due to a sulfinyl moiety in the 7β-side chain. Infrared Spectrum (Nujol):3200, 1795, 1720 cm$^{-1}$ For identification of the each isomer, the carboxylic acids were converted to the corresponding benzhydryl esters by a usual manner with diphenyl diazomethane, and isomers were separated by preparative tlc using silica gel plate, which was developed with benzeneethyl acetate (1:1).
  Nuclear Magnetic Resonance Spectrum of one isomer (DMF-d$_7$) δ ppm:
  3.66 (2H, singlet),
  3.92 (3H, singlet),
  4.25 and 4.41 (2H, AB-quartet, J=14 Hz),
  4.53 (1H, doublet, J=4.5 Hz),
  5.50 (1H, doublet of doublet), J=4.5 and 9.0 Hz),
  6.98 (1H, singlet), 7.25–8.50 (14H, multiplet).
  Infrared Spectrum (Nujol):3200, 1785, 1730 cm$^{-1}$
  Nuclear Magnetic Resonance Spectrum of another isomer (DMF-d$_7$) δ ppm:
  3.80 (2H, singlet),
  3.95 (3H, singlet)
  4.31 and 4.42 (2H, AB-quartet, J=14 Hz)
  5.16 (1H, doublet, J=4.50 Hz),
  5.35 (1H, doublet of doublet, J=4.50 and 9.0 Hz),
  6.95 (1H, singlet) 7.25–8.51 (14H, multiplet).
  Infrared Spectrum (Nujol):3200, 1785, 1730 cm$^{-1}$.

REFERENTIAL EXAMPLE 5

3-Methyl-7β-pentachlorophenylsulfenylamino-3-cephem-4-carboxylic acid t-butyl ester To a solution of 1.35 g. of 7β-amino-3-cephem-4-carboxylic acid t-butyl ester and 870 mg. of propylenoxide in 20 ml. of methylene chloride was added dropwise a solution of 1.58 g. of pentachlorophenylsulfenyl chloride in 10 ml. of methylene chloride at 0° C. After the addition the reaction mixture was stirred at room temperature for 1 hour. The solution was diluted with 50 ml. of methylen chloride and washed with water three times. The dried solution (Na₂SO₄) was evaporated under diminished pressure to give an oil, which was chromatographed on 33 g. of silica gel. Elution with benzene and evaporation afforded 1.115 g. of 3-methyl-7β-pentachlorophenylsulfenylamino-3-cephem-4-carboxylic acid t-butyl ester as a foam. Trituration with i-propyl ether gave a sample melting at 156°-158° C.

Nuclear Magnetic Resonance Spectrum (CDCl₃+D₂O) δ ppm:
  1.49 (9H, singlet),
  2.03 (3H, singlet),
  3.13 and 3.36 (2H, AB-quartet, J=18 Hz),
  4.79 (1H, doublet, J=4.5 Hz),
  4.89 (1H, doublet, J=4.5 Hz).

Infrared Spectrum (Nujol):3200, 1790, 1720 cm⁻¹.

REFERENTIAL EXAMPLE 6

7β-amino-7α-methoxy-3-methyl-3-cephem-4-carboxylic acid tert-butyl ester

In a mixture of 2 ml. of methanol and 0.4 ml. of acetic acid was dissolved 399 mg. of sodium iodide and 2 ml. of methylene chloride solution containing 102.4 mg. of 7α-methoxy-7β-paranitrophenylsulfenylamino-3-cephem-4-carboxylic acid tert-butyl ester was added to the solution under ice cooling. After mixture was stirred under ice cooling for 20 minutes, white crystals precipitated and the solution turned brown. In the solution, the starting material was not detected by thin-layer-chromatography (development system: benzene-ethyl acetate (3:1)). Immediately thereafter the reaction was stopped by placing the solution in a bath of −78° C. and 20 ml. of ethyl acetate was added to the solution. After the reaction mixture was quickly washed with an aqueous solution of sodium bicarbonate, an aqueous solution of sodium thiosulfate and water successively, and dried, the solvent was removed by evaporation under reduced pressure. The thus obtained residue was purified by preparative silica gel thin-layer-chromatography (20×20 cm., thickness: 0.2 cm., development system: benzene-ethyl acetate (3:1)) to isolate a compound having a Rf value of around 0.70, thereby yielding 36 mg. of 7β-amino-7α-methoxy-3-methyl-3-cephem-4-carboxylic acid tert-butyl ester.

Nuclear Magnetic Resonance Spectrum (CDCl₃) δ ppm:
  1.52 (9H, singlet), 2.13 (3H, singlet),
  1.96-2.40 (2H, broad singlet), 3.19 (2H, singlet),
  3.48 (3H, singlet), 4.79 (1H, singlet).

REFERENTIAL EXAMPLE 7

7α-Methoxy-3-methyl-7β-phenoxyacetamido-3-cephem-4-carboxylic acid tert-butyl ester In a mixture of 1 ml. of methylene chloride and 1 ml. of methanol was dissolved 33.1 mg. of 7α-methoxy-3-methyl-7β-paranitrophenylsulfenylamino-3-cephem-4-carboxylic acid tert-butyl ester. To the solution were added 0.1 ml. of phenyl mercaptan and 0.04 ml. of triethyl amine, and the mixture was stirred for 15 hours at room temperature. After completion of the reaction, ethyl acetate was added and the mixture was concentrated. After dissolving the residue in 2 ml. of methylene chloride, 0.2 ml. of diethylaniline was added at −40° C. and then 0.2 ml. of phenoxyacetyl chloride to the solution. Thereafter the solution was stirred at −20° C. for 1 hour. After completion of the reaction, ethyl acetate was added to the solution. The resulting solution was washed successively with an aqueous solution of potassium hydrogen sulfate, an aqueous solution of sodium bicarbonate and water, and the solvent was removed by evaporation under reduced pressure. The thus obtained residue was purified by preparative silica gel thin-layer-chromatography (thickness: 0.2 cm., 7×10 cm., development system: benzene-ethyl acetate (5:1)) to isolate 27 mg. of 7α-methoxy-3-methyl-7β-phenoxyacetamido-3-cephem-4-carboxylic acid tert-butyl ester. The thus yielded compound included a little amount of the Δ²-isomer.

Nuclear Magnetic Resonance Spectrum (CDCl₃) δ ppm:
  1.53 (9H, singlet),
  2.12 (3H, singlet),
  3.08 and 3.33 (2H, AB-quartet, J=18 Hz),
  3.55 (3H, singlet),
  4.60 (2H, singlet),
  5.07 (1H, singlet),
  6.80-7.53 (6H, multiplet).

REFERENTIAL EXAMPLE 8

7α-Methoxy-3-methyl-7β-phenoxyacetamido-3-cephem-4-carboxylic acid tert-butyl ester In a mixture of 1 ml. of methylene chloride and 1 ml. of methanol was dissolved 30 mg. of 7α-methoxy-3-methyl-7β-paranitrophenylsulfenylamino-3-cephem-4-carboxylic acid tert-butyl ester. After adding 0.1 ml. of hexamethylphosphoroustriamide and 0.04 ml. of triethylamine, the mixture was stirred at room temperature for 15 hours. After completion of the reaction, ethyl acetate was added and the solution was concentrated. After dissolving the residue in 2 ml. of methylene chloride, 0.2 ml. of diethylaniline was added at −40° C. and then was added 2 ml. of phenoxyacetyl chloride. The resulting solution was stirred for 1 hour at −20° C. After completion of the reaction, ethyl acetate was added. The resulting solution was successively washed with an aqueous solution of potassium hydrogen sulfate, an aqueous solution of sodium bicarbonate and water, and dried. The solvent was removed by evaporation under reduced pressure. The thus obtained residue was purified by preparative thin-layer-chromatography (thickness: 0.2 cm., 7×10 cm., development system: benzene-ethyl acetate (5:1)) to isolate 26 mg. of 7α-methoxy-3-methyl-7β-phenoxyacetamido-3-cephem-4-carboxylic acid tert-butyl ester. This compound included a little amount of the Δ²-isomer.

REFERENTIAL EXAMPLE 9

7α-Methoxy-3-methyl-7β-phenoxyacetamido-3-cephem-4-carboxylic acid tert-butyl ester After 101 mg. of 7α-methoxy-3-methyl-7β-paranitrophenylsulfenylamino-3-cephem-4-carboxylic acid tert-butyl ester was dissolved in 5 ml. of acetonitrile, 0.10 ml. of phenoxyacetyl chloride was added under ice cooling and the reaction was conducted for 30 minutes. After completion of the reaction, 1.0 ml. of ethyl acetate was added and the resulting solution was washed successively with an aqueous solution of sodium bicarbonate and water. After drying the solution, the solvent was removed by evaporation under reduced pressure. The thus yielded residue was purified by preparative silica gel thin-layer-chromatography (thickness: 0.2 cm., 10×20 cm., development system:benzene-ethyl acetate (5:1)) to isolate 5 mg. of 7α-methoxy-3-methyl-7β-phenoxyacetamido-3-cephem-4-carboxylic acid tert-butyl ester.

What is claimed is:

1. A process for the preparation of a compound having the formula

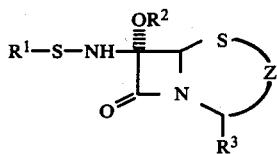

wherein R[1] represents phenyl group substituted with from one to 5 members selected from nitro, cyano, halogen or alkoxycarbonyl having 1–4 carbon atoms in the alkyl moiety; R[2] represents an alkyl group having 1–4 carbon atoms; R[3] represents carboxyl group or a protected carboxyl group selected from the group consisting of an alkoxycarbonyl having 1–4 carbon atoms in the alkoxy moiety, halogenoalkoxycarbonyl having 1–4 carbon atoms in the alkoxy moiety, benzyloxycarbonyl and benzyloxycarbonyl substituted with nitro or methoxy in the phenyl group, diphenylmethoxycarbonyl, trialkylsilyloxycarbonyl having 1–4 carbon atoms in each alkyl moiety, phenacyloxycarbonyl and phenacyloxycarbonyl substituted with halogen or nitro, acyloxycarbonyl, halogenoacyloxycarbonyl, dialkylphosphinooxycarbonyl having 1–4 carbon atoms in the alkyl moiety, dihalogenophosphinooxycarbonyl, and aminocarbonyl; Z represents a fragment of the formula

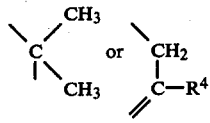

wherein R[4] is selected from the group consisting of alkyl having 1–4 carbon atoms, alkoxy having 1–4 carbon atoms, halogen, carbamoyloxymethyl, alkanoyloxymethyl having 1–4 carbon atoms in the alkyl moiety, benzoyloxymethyl, and heterocyclic thiomethyl selected from the group consisting of tetrazolyl, 1-alkyltetrazolyl-, 1-carboxyalkyltetrazolyl-, 1-alkoxycarbonylalkyltetrazolyl-, 1-sulfoalkyltetrazolyl-, 1-aminosulfonylalkyltetrazolyl-, 1-mono- or dialkylaminosulfonylalkyltetrazolyl-, 1-aminoalkyltetrazolyl-, 1-mono-or dialkylaminoalkyltetrazolyl-, isoxazolyl-, imidazolyl-, thiazolyl-, triazolyl-, thienyl-, thiadiazolyl-, methylthiadiazolyl-, pyrimidinyl- and pyridylthiomethyl, and a pharmaceutically acceptable salt thereof; which comprises reacting a compound having the formula

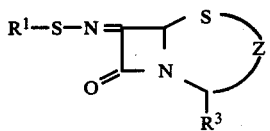

with an alcohol having the formula

R[2]OH in the presence of a compound selected from the group consisting of alkali metal hydroxides, alkaline earth metal hydroxides, alkali metal carbonates, and alkali metal alkoxides.

2. The process of claim 1, wherein the alkali metal alkoxide is selected from the group consisting of lithium methoxide, potassium methoxide, sodium methoxide and potassium tertiary butoxide.

3. A process for the preparation of a compound having the formula

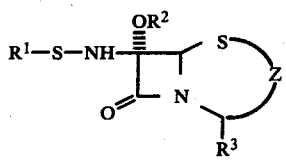

wherein R[1] represents phenyl group substituted with from one to 5 members selected from nitro, cyano, halogen or alkoxycarbonyl having 1–4 carbon atoms in the alkyl moiety; R[2] represents an alkyl group having 1–4 carbon atoms; R[3] represents carboxyl group or a protected carboxyl group selected from the group consisting of an alkoxycarbonyl having 1–4 carbon atoms in the alkoxy moiety, halogenoalkoxycarbonyl having 1–4 carbon atoms in the alkoxy moiety, benzyloxycarbonyl and benzyloxycarbonyl substituted with nitro or methoxy in the phenyl group, diphenylmethoxycarbonyl, trialkylsilylcarbonyl having 1–4 carbon atoms in each alkyl moiety, phenacyloxycarbonyl and phenacyloxycarbonyl substituted with halogen or nitro, acyloxycarbonyl, halogenoacyloxycarbonyl, dialkylphosphinooxycarbonyl having 1–4 carbon atoms in the alkyl moiety; dihalogenophosphinooxycarbonyl, and aminocarbonyl; Z represents a fragment of the formula

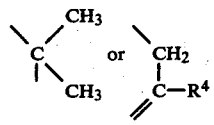

wherein R[4] is selected from the group consisting of alkyl having 1–4 carbon atoms, alkoxy having 1–4 carbon atoms, halogen, carbamoyloxymethyl, alkanoyloxymethyl having 1–4 carbon atoms in the alkyl moiety, benzoyloxymethyl, and heterocyclic thiomethyl selected from the group consisting of tetrazolyl, 1-alkyltetrazolyl-, 1-carboxyalkyltetrazolyl-, 1-alkoxycarbonylalkyltetrazolyl-, 1-sulfoalkyltetrazolyl-, 1-aminosulfonylalkyltetrazolyl-, 1-mono- or dialkylaminosulfonylalkyltetrazolyl-, 1-aminoalkyltetrazolyl-, 1-mono- or dialkylaminoalkyltetrazolyl-, isoxazolyl-, imidazolyl-, thiazolyl-, triazolyl-, thienyl-, thiadiazolyl-, methylthiadiazolyl-, pyrimidinyl- and pyridylthiomethyl, and a pharmaceutically acceptable salt thereof; which comprises reacting a compound having the formula

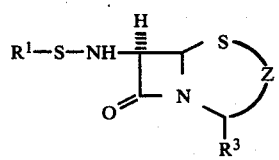

(II)

with metal dioxide to form the compound having the formula

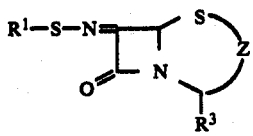 (III)
and reacting the latter compound III with an alcohol having the formula
R²OH     IV
in the presence of a compound selected from the group consisting of alkali metal hydroxides, alkaline earth metal hydroxides, alkali metal carbonates and alkali metal alkoxides to form said compound I.
4. The process of claim 3, wherein the metal oxide is manganese dioxide.
* * * * *